(12) United States Patent
Sunvold et al.

(10) Patent No.: US 6,306,430 B1
(45) Date of Patent: Oct. 23, 2001

(54) PROCESS FOR DECREASING ADIPOSITY USING VITAMIN A AS A DIETARY SUPPLEMENT

(75) Inventors: Gregory D. Sunvold, Eaton; Michael G. Hayek, Dayton, both of OH (US)

(73) Assignee: The Iams Company, Dayton, OH (US)

( * ) Notice: Subject to any disclaimer, the term of this patent is extended or adjusted under 35 U.S.C. 154(b) by 0 days.

(21) Appl. No.: 09/288,873

(22) Filed: Apr. 9, 1999

Related U.S. Application Data
(60) Provisional application No. 60/081,969, filed on Apr. 16, 1998.

(51) Int. Cl.$^7$ .......................... A29K 1/165; A29K 31/07
(52) U.S. Cl. ..................... 424/442; 424/438; 426/53; 426/73; 426/805; 514/725; 514/909
(58) Field of Search ..................... 424/442, 438; 514/725, 909; 426/2, 53, 73, 805

(56) References Cited

U.S. PATENT DOCUMENTS
5,501,857 * 3/1996 Zimmer ................................. 424/438
6,013,622 * 1/2000 Bruno et al. ............................. 514/2

OTHER PUBLICATIONS
Morrison Feeds & Feeding pp. 742,743,752,753,1148,1149, 1954.*
Jones *Veterinary Pharmacology & Therapeutics* p. 884, 1965.*
Alvarez et al., "A novel Regulatory Pathway of Brown Fat Thermogenesis", *J. of Biol. Chem.*, pp. 5666–5673, 1995.
Wolf, "A Regulatory Pathway of Thermogenesis in Brown Fat Through Retinoic Acid", *Nutrition Reviews*, vol. 53, No. 8, pp. 230–231, 1995.
Cassard–Doulcier et al., "In Vitro Interactions in between Nuclear Proteins and Uncoupling Protein Gene Promoter Reveal Several Putative Transactivating Factors Including Ets1, Retinoid X Receptor, Thyroid Hormone Receptor, and a CACCC Box–binding Protein", *J. of Biol. Chem.*, pp. 24335–24342, 1994.

Facchini et al., "Relatin between dietary vitamin intake and resistance to insulin–mediated glucose Disposal in healthy volunteers [1–3]", *American J Clin Nutr*, pp. 946–949, 1996.

Puigserver et al., "In vitro and in vivo induction of brown adipocyte uncoupling protein (thermogenin) by Retinoic acid", *Biochem J.*, pp. 827–833, 1996.

Suryawan et al., "Effect of Retinoic Acid on Differentiation of Cultured Pig Preadipocytes", 1997, *J. Anim. Sci.*, pp. 112–117, 1997.

Kumar et al., "Differential effects of retinoic acid on uncoupling protein–1 and leptin gene expression", *J. Endocrinol.*, pp. 1–7, 1998.

Abstract, Kumar et al., "Differential effects of retinoic acid uncoupling protein–1 and leptin gene Expression", *J Endocrinol*, May 1998.

Abstract, Scarpace et al., "Thermoregulatin with age: role of thermogenesis and uncoupling protein Expression in brown adipose tissue", *Proc Soc Exp Biol Med*, Feb. 1994.

Abstract, Chomczynksi et al., "Single–step method of RNA isolation by acid guanidinium thiocyanate–phenol–chloroform extraction", *Anal Biochem*, Apr. 1987.

* cited by examiner

*Primary Examiner*—Neil S. Levy
(74) *Attorney, Agent, or Firm*—Killworth, Gottman, Hagan & Schaeff, L.L.P.

(57) ABSTRACT

A process is provided for reducing adiposity in an animal such as a companion animal by feeding the animal an effective amount of Vitamin A for a time sufficient to reduce adiposity in the animal. Preferably, the such effective amount comprises from about 50,000 IU to about 1,000,000 IU of Vitamin A per kilogram of diet. Such an effective amount provides sufficient Vitamin A to decrease accumulation of body fat, increase UCP1 levels, and decrease serum leptin levels in the animal.

9 Claims, 3 Drawing Sheets

PROCESS FOR DECREASING ADIPOSITY USING VITAMIN A AS A DIETARY SUPPLEMENT

CROSS REFERENCE TO RELATED APPLICATIONS

This application claims the benefit of U.S. provisional application Ser. No. 60/081,969, filed Apr. 16, 1998.

BACKGROUND OF THE INVENTION

This invention relates to a pet food supplement and process for decreasing adiposity in animals, and more particular, to a pet food supplement which includes beneficial amounts of Vitamin A in the animal's diet.

Obesity is extremely prevalent in many species including humans, dogs, cats and horses. For example, 20 to 40% of dogs and humans have been estimated to be overweight or obese. Traditionally, high fiber diets have been used to combat obesity. However, high fiber diets are often associated with several undesirable side effects including decreased palatability of food, increased stool volume, increased defecation frequency, poor skin and hair, improper mineral balance, and decreased food digestibility.

An alternative way to control weight is to induce energy expenditure in an individual. Changing the metabolism of fat tissue may regulate energy expenditure. Fat tissue is generally categorized as white adipose tissue (WAT) or brown adipose tissue (BAT). Energy expenditure, in part, is regulated by BAT. Within BAT is uncoupling protein (UCP)-1. UCP1 is a proton carrier that, upon activation, causes the uncoupling of respiration from oxidative phosphorylation, thus causing increased energy expenditure from the body through heat generation. It is known that all-trans-retinoic acid (RA), one of the active metabolites of vitamin A, can induce the gene expression of UCP1 in brown adipose tissue (BAT) of rats. Due to its function in energy expenditure and energy balance, BAT has been implicated to play an important role in the control of obesity.

Another gene that has been recently identified to play an important role in energy homeostasis is the ob gene. The product of the ob gene, leptin, is primarily produced in white adipose tissue (WAT). Leptin is believed to be the signal for the level of adiposity, and this hormone both suppresses food intake and increases energy expenditure. However, there have been few studies on diet compositions designed to induce energy expenditure as a means to control obesity.

Accordingly, there is still a need in the art for decreasing adiposity in animals including companion animals such as dogs, cats, and horses.

SUMMARY OF THE INVENTION

The present invention addresses the need for reducing adiposity by providing a process for feeding an animal an effective amount of Vitamin A for a time sufficient to reduce adiposity in the animal. By "reduce adiposity," we mean that for a given animal ingesting a given amount of food, the percentage of body fat in the animal will be lower when the animal is provided with the effective amount of Vitamin A as compared with an animal ingesting the same amount of food, but without Vitamin A supplementation. The Vitamin A may be provided to the animal either as a supplement or contained in a diet fed to the animal. Such a supplement may be in the form of a pill or capsule, a treat or biscuit, or any other edible form. By "diet" we mean the food or drink regularly consumed by the animal.

When supplied as a supplement, the supplement preferably comprises from about 50,000 IU to about 1,000,000 IU of Vitamin A per kilogram of diet, more preferably, from about 50,000 IU to about 500,000 IU of Vitamin A per kilogram of diet, and most preferably, from about 50,000 IU to about 150,000 IU of Vitamin A per kilogram of diet. These amounts are over and above the amount of Vitamin A which may be present in other components of the diet of the animal.

The supplement is preferably fed to the animal in an amount of about 50,000 IU to about 1,000,000 IU of Vitamin A per day (based on a diet of 1,000 g per day), or about 5,000 IU to about 100,000 IU of Vitamin A per day (based on a diet of 100 g per day). The Vitamin A may be provided in the supplement as retinol, and provides sufficient Vitamin A to result in a reduction in adiposity of the animal.

The supplement may be fed to companion animals including dogs, cats, and horses. In addition to reducing adiposity in animals, the supplement may also be used to increase UCP1 gene expression, suppress leptin gene expression, and suppress serum leptin levels. The supplement may also be used to help prevent obesity, promote weight loss, and may also be used to minimize age-related increases in body fat and diabetes-associated increases in body fat.

Accordingly, it is a feature of the invention to provide a pet food supplement or diet and process for reducing adiposity by providing an effective amount of Vitamin A in the diet of the animal. This, and other features and advantages of the present invention, will become apparent from the following detailed description, accompanying drawings, and appended claims.

DETAILED DESCRIPTION OF THE PREFERRED EMBODIMENTS

Figure 1:
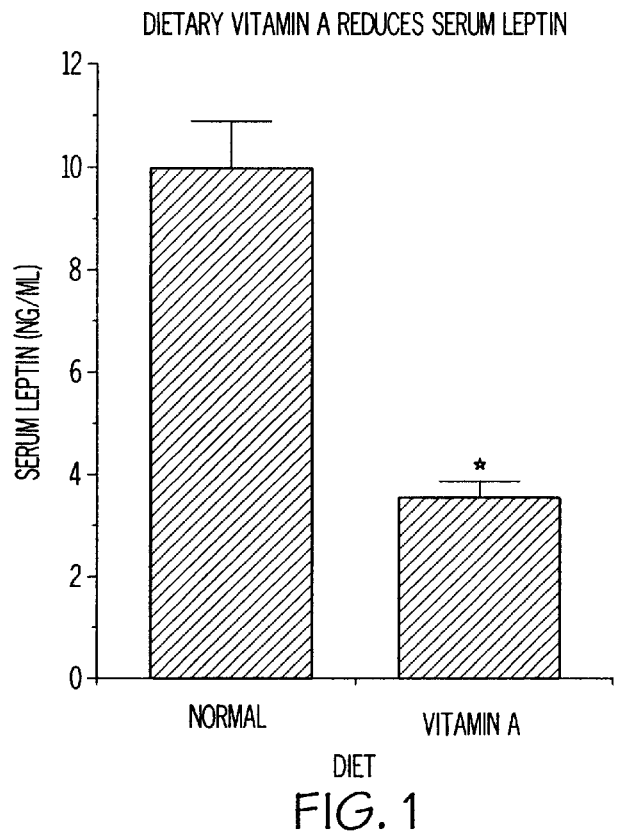
FIG. 1 is a graph of serum leptin levels (ng/ml) in rats fed a normal diet and a vitamin A supplemented diet for 8 weeks.

The present invention uses a supplement or diet which contains a source of Vitamin A in an amount of between about 50,000 IU to about 1,000,000 IU of Vitamin A per kilogram of diet.

Feeding animals effective amounts of Vitamin A results in a reduction in adiposity (as compared with an animal fed the same diet but without Vitamin A supplementation), an increase in β3-adrenergic stimulated oxygen consumption, an increase in UCP1 gene expression in BAT, and suppression of leptin gene expression and serum leptin levels. The reduction in adiposity is surprising because the suppression of leptin gene expression would be expected to promote obesity by reducing leptin levels in the animal.

The Vitamin A may be included in a diet which can comprise any suitable pet food formulation which also provides adequate nutrition for the animal. For example, a typical canine diet for use in the present invention may contain about 18–40% crude protein, about 4–30% fat, and about 4–20% total dietary fiber. However, no specific ratios or percentages of these or other nutrients are required. The Vitamin A, preferably in the form of retinol, may be blended with such pet food formulation such that the diet includes from about 50,000 IU to about 1,000,000 IU of Vitamin A per kilogram of diet.

In order that the invention may be more readily understood, reference is made to the following examples which are intended to illustrate the invention, but not limit the scope thereof.

EXAMPLE 1

Male F-344×BN rats of 5 months of age were obtained from Harlan Sprague-Dawley (Indianapolis, Ind.). Upon arrival, rats were examined and remained in quarantine for one week. Animals were cared for in accordance with the principles of the Guide to the Care and Use of Experimental Animals. Rats were housed individually with a 12:12 h light-dark cycle (07:00 to 19:00 hr). Ambient temperature was 26° C., thermoneutrality for these rats.

Rats were fed a diet containing either, 8,643 IU retinol/kg diet (normal diet) or 430,431 IU retinol/kg diet (vitamin A supplemented diet) for a period of 8 weeks. Food and water were provided ad libitum. Body weights and food intake were recorded weekly. Basal whole body oxygen consumption was measured before starting the diet and then after week 3, 6 and 8 on the diet. At the end of 8 weeks, half the rats from each group were challenged with a single dose of the β3 adrenergic specific agonist, CGP-12177 (prepared in pyrogen-free saline, available from Ciba-Geigy, Summit, N.J.) (0.75 mg/kg, i.p.) or saline. The stimulated whole body oxygen consumption was measured and the animals sacrificed 4 hours after injection.

Oxygen Consumption $O_2$ consumption was assessed on up to four rats simultaneously with an Oxyscan analyzer (OXS-4; Amniotic Electronics, Columbus, Ohio). All experiments were performed on conscious unanesthetized rats during the light phase of the light-dark cycle. Flow rates were 2 L/min with a 30 second sampling time at 5 minute intervals. The temperature was maintained at 26° C. Results were expressed on a mass-dependent basis (ml/min/$g^{0.67}$). The cumulative increase in the CGP12177-stimulated oxygen consumption was calculated as the average increase over baseline from 30 min to 110 min, post injection.

Tissue Harvesting

Rats were sacrificed by cervical dislocation under 90 mg/kg pentobarbital anesthetic. Blood was collected in Vacutainer SST tubes (Becton Dickinson, Franklin Lakes, N.J.) via cardiac puncture using an 18-gauge needle followed by perfusion with 60 ml of 0.9% saline. Interscapular brown adipose tissue (IBAT), perirenal white adipose tissue (PWAT), retroperitoneal white adipose tissue (RTWAT), epididymal white adipose tissue (EWAT) and liver were excised, weighed, and rapidly stored in liquid nitrogen. The tissues were stored at −70° C. until analysis.

Determination of Adiposity Levels

Adiposity was determined by the adiposity index (the sum of the weights of perirenal WAT, retroperitoneal WAT, and epididymal WAT divided by body weight×100). This adiposity measure is highly correlated with the percentage of body fat.

Leptin Radioimmunoassay

Serum leptin levels were measured with a rat leptin radioimmunoassay kit (Linco Research, St. Charles, Mo.).

Serum and Liver Retinol

Total retinol from serum (400 μL) and liver (500 μg) were extracted by addition of 1 ml hexane with 0.01% BHT in the cold. The hexane extraction was repeated twice and the extracts pooled and evaporated to dryness under nitrogen. Extracted lipids were resuspended in hexane methanol (1:9) solution containing 0.01% BHT and analysis for retinol by HPLC (Furr et al. 1984).

UCP1 and Leptin mRNA Levels

Total cellular RNA was extracted using a modification of the method described in Chomczynski and Sacchi, "Single step method of RNA isolation by acid guanidinium thiocyanate-phenolchloroform extraction", *Analytical Biochemistry* 162:156–159 (1987). The integrity of the isolated RNA was verified using 1% agarose gels stained with ethidium bromide. The RNA was quantified by spectrophotometric absorption at 260 nm using multiple dilutions of each sample.

The probe to detect leptin mRNA was a 33-mer antisense oligonucleotide (5'GGTCTGAGGCAGGGAGCAGCTCTTGGAGAA GGC), end-labeled using terminal deoxynucleotidyl transferase. The oligonucleotide was based on a region of the mRNA downstream from the site of the primary mutation in ob/ob mice and synthesized at the University of Florida core facility and verified by Northern analysis as described in Li et al, "Beta(3)-adrenergic-mediated suppression of leptin gene expression in rats," *American Journal of Physiology* 272 (1997). The full length cDNA clone for uncoupling protein-1 (UCP1) was provided by Dr. Leslie Kozak, Jackson Laboratory, Bar Harbor, Me. and verified by Northern analysis, as described in Scarpace et al., "Thermoregulation with age: Role of thermogenesis and uncoupling protein expression in brown adipose tissue", *Proceedings of the Society for Experimental Biology and Medicine* 205:154–161(1994). The UCP1 cDNA probe and the full length human β-actin cDNA probe (Clontech, Palo Alto, Calif.) and the mouse LPL cDNA clone (ATCC. Rockville. Md.) were random prime labeled using Prime-a-Gene (Promega).

For dot-blot analysis, multiple concentrations of RNA were immobilized on nylon membranes using a dot-blot apparatus (Biorad, Richmond, Calif.). The membranes were baked at 80° C. for 2 hrs. The baked membranes were prehybridized using 25 mM potassium phosphate, 750 mM NaCl, 75 mM Na citrate, 5×Denhardt's solution, 50 μg/ml denatured salmon sperm DNA, and 50% formamide. After incubation for 14–16 hrs. at 42° C., the membranes were hybridized with $^{32}$P labeled probes in the prehybridization buffer plus 10% dextran sulfate. After hybridization for 14–16 hr at 42° C., the membranes were washed and exposed to a phosphor imaging screen for 48 hrs. The latent image was scanned using a Phosphor Imager (Molecular Dynamic, Sunnyvale, Calif.) and analyzed by Image Quant Software (Molecular Dynamics). Intensities per $\mu$g total cellular RNA were calculated by comparison to internal laboratory standards of WAT or BAT total RNA present on each nylon membrane.

Data Analysis

One way or two way analysis of variance was applied where appropriate. When main effect was significant, Scheffe's post hoc comparison was applied.

RESULTS

Weight Gain Food Intake, Body Fat and Vitamin A Status

At the end of the 8 week period on the normal or vitamin A supplemental diet, the vitamin A status of the animals was evaluated by determining the concentration of retinol in serum and liver. Whereas, the serum retinol concentrations were unaffected by vitamin A supplementation, the liver retinol concentration was 10.8 fold greater in the vitamin A supplemented group, compared with controls (Table 1). This relative difference in liver retinol was nearly equal to the 13.75 fold difference in the vitamin A contents of the normal and supplemented diets. The vitamin A supplemented rats, however, did not show any signs of vitamin A toxicity, including depressed growth, occasional bleeding from the nose, or partial paralysis of the legs.

TABLE 1

Serum and liver retinol levels in control and dietary Vitamin A supplemented rats

| Diet | Retinol | |
|---|---|---|
| | Serum (ng/ml) | Liver (ng/ml) |
| Normal | 34 ± 1 | 498 ± 28 |
| Vitamin A Supplemented | 32 ± 1 | 5406 ± 163* |

Data represent mean ± SE of 15 (normal diet) or 16 (Vitamin A supplemented diet) rats.
*p = 0.0001 for difference from rats fed the normal diet by one-way ANOVA.

Pre-diet and post-diet body weights as well as the gain in body weight in the control and in the vitamin A supplemented groups was similar (Table 2). Food intake was also unchanged by dietary vitamin A supplementation (Table 2).

TABLE 2

Food intake and body weight parameters and adiposity in control and dietary Vitamin A supplemented rats

| | Diet | |
|---|---|---|
| | Normal | Vitamin A supplemented |
| Daily food intake (g/day) | 18.1 ± 0.3 | 18.1 ± 0.4 |
| Pre diet body weight (g) | 328 ± 6 | 326 ± 5 |
| Post diet body weight (g) | 390 ± 8 | 386 ± 7 |
| Body weight gain (g) | 61.8 ± 5.1 | 59.3 ± 5.2 |
| BAT weight (mg) | 411 ± 12 | 430 ± 20 |

TABLE 2-continued

Food intake and body weight parameters and adiposity in control and dietary Vitamin A supplemented rats

| | Diet | |
|---|---|---|
| | Normal | Vitamin A supplemented |
| PWAT weight (mg) | 1.49 ± 0.06 | 1.23 ± 0.07* |
| RTWAT weight (mg) | 3.80 ± 0.10 | 3.53 ± 0.13 |
| EWAT weight (mg) | 2.98 ± 0.10 | 2.62 ± 0.09* |
| Adiposity index | 2.09 ± 0.04 | 1.91 ± 0.04* |

Data represent mean ± SE of 15 (control) or 16 (Vitamin A supplemented) rats.
*p = 0.005 (PWAT), p = 0.013 (EWAT) or p = 0.004 (Adiposity index) for difference from rats fed the normal diet by one-way ANOVA.

In contrast, there was a significant decrease in PWAT and EWAT weight in the rats fed the vitamin A supplemented compared with the normal diet (Table 2). In rats on the vitamin A supplemented diet, there was a 17% reduction in the weight of PWAT, and 12% reduction in the weight of EWAT. The weight of the RTWAT, a third WAT depot was unchanged (Table 2). Overall, there was a significant decrease in the adiposity index [(sum of three WAT depots divided by the body weight)×100], in the rats fed the vitamin A supplemented diet (Table 2). In contrast, there were no changes in BAT weights, upon vitamin A supplementation (Table 2).

Serum Leptin Levels and Leptin mRNA Levels in PWAT

In general, serum leptin levels reflect body fat content, thus the decrease in adiposity in the dietary vitamin A supplemented rats should result in a corresponding decrease in serum leptin. Surprisingly, the decrease in serum leptin in the vitamin A supplemented rats was 65%, much greater than predicted from the 9% decrease in the adiposity index (FIG. 1). This dramatic decrease in serum leptin suggests leptin synthesis was inhibited.

Figure 2:
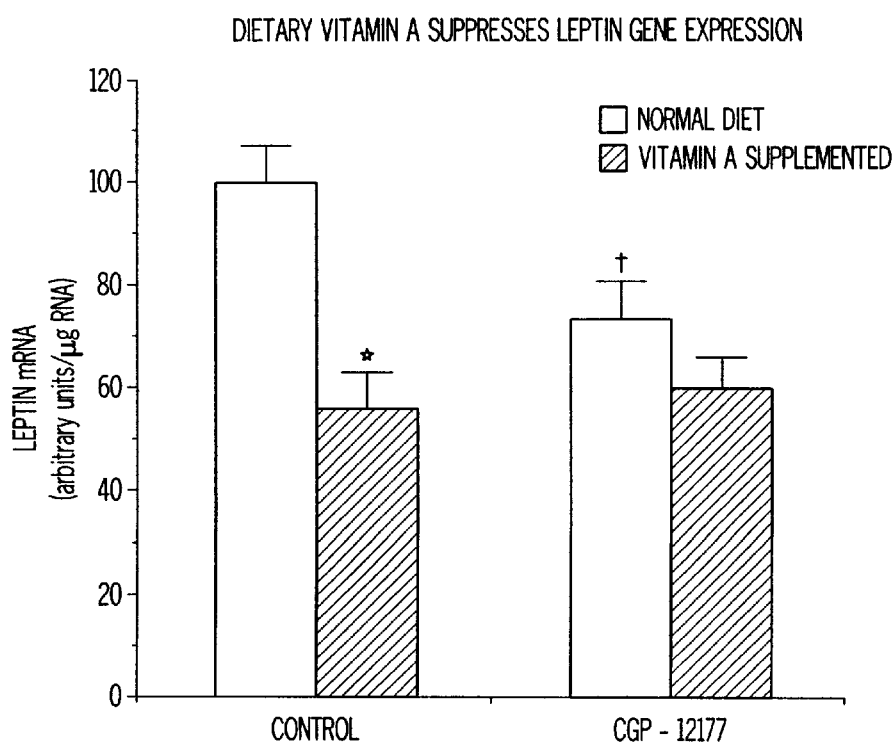
FIG. 2 is a graph of leptin mRNA levels (arbitrary units/$\mu$g RNA) in rats fed a normal diet or a Vitamin A supplemented diet.

To assess if there was a suppression of leptin mRNA levels in PWAT upon vitamin A supplementation, leptin mRNA levels were compared in the control animals on the vitamin A supplemented and control diet. There was a 44% suppression of leptin mRNA levels per unit of total RNA in rats on the vitamin A supplemented, compared with the normal diet (FIG. 2). β3-adrenergic agonists also inhibit leptin gene expression. To compare the suppression of leptin gene expression by the β3-adrenergic agonist, CGP-12177 with dietary vitamin A supplementation, at the end of the 8 week dietary regimen, each dietary group was administered CGP-12177 and leptin mRNA levels determined in PWAT 4 hr later. As expected, the β3-adrenergic agonist suppressed leptin mRNA levels by 27% in the rats on the normal diet (FIG. 2). In contrast, in the vitamin A supplemented group, administration of CGP-12177 had no further effect on leptin mRNA levels, compared with the saline treated controls on the same diet (FIG. 2). There were no changes in the levels of β actin mRNA in BAT in the saline or CGP-12177 treated animals in the two dietary groups (Table 3).

TABLE 3

UCP2, $\beta_3$-adrenergic receptor and $\beta$-actin transcript levels
with and without CGP-12177 administration in rats fed a
normal or Vitamin A supplemented diet

| | MRNA levels (arbitrary units) | | | |
|---|---|---|---|---|
| | Normal Diet | | Vitamin A supplemented diet | |
| Transcript | Saline | CGP-12177 | Saline | CGP-12177 |
| PWAT: | | | | |
| UCP2 | 100 ± 11 | 109 ± 10 | 110 ± 14 | 110 ± 10 |
| $\beta_3$AR | 100 ± 9.2 | 105 ± 6.0 | 84.0 ± 13.1 | 112 ± 11 |
| BAT: | | | | |
| UCP2 | 100 ± 13 | 93.4 ± 12.2 | 103 ± 5.2 | 94 ± 8.9 |
| $\beta_3$AR | 100 ± 4 | 50.9 ± 3.3* | 104 ± 15.6 | 59.8 ± 7.9* |
| $\beta$-actin | 100 ± 10 | 98.6 ± 7.4 | 86.1 ± 7.2 | 93.8 ± 8.0 |

Data represent mean ± SE of 6–7 rats per group. $\beta_3$AR is $\beta_3$-adrenergic receptor.
*p = 0.0001 for difference between CGP-12177 administration and control rats by two-way ANOVA. p = 0.0001 (normal diet) and p = 0.003 (vitamin A supplemented diet) for difference between CGP-12177 administration and corresponding control rats.

Oxygen Consumption

The decrease in adiposity with dietary vitamin A supplementation without a change in food intake suggests an increase in energy expenditure. To assess if there was enhanced energy expenditure upon vitamin A supplementation, basal whole body oxygen consumption was measured before starting the diet and at weeks 3, 6 and 8 on the diet. There was no change in basal oxygen consumption between the two dietary groups (normal and vitamin A supplemented) at either week 3, 6, or 8 after starting the diet (Table 4).

TABLE 4

Basal whole body oxygen consumption over 8 weeks
in rats fed the normal and Vitamin A supplemental diets

| | Oxygen consumption (ml/min/kg$^{0.67}$) | |
|---|---|---|
| | Normal diet | Vitamin A supplemented |
| Pre-diet | 12.7 ± 0.6 | 12.8 ± 0.9 |
| Week 3 | 11.0 ± 0.1 | 10.8 ± 0.1 |
| Week 6 | 10.6 ± 0.2 | 10.4 ± 0.1 |
| Week 8 | 10.4 ± 0.2 | 10.2 ± 0.2 |

Data represent mean ± SE of 16 rats in each group. Oxygen consumption was assessed over a one hour period.

Figure 3:
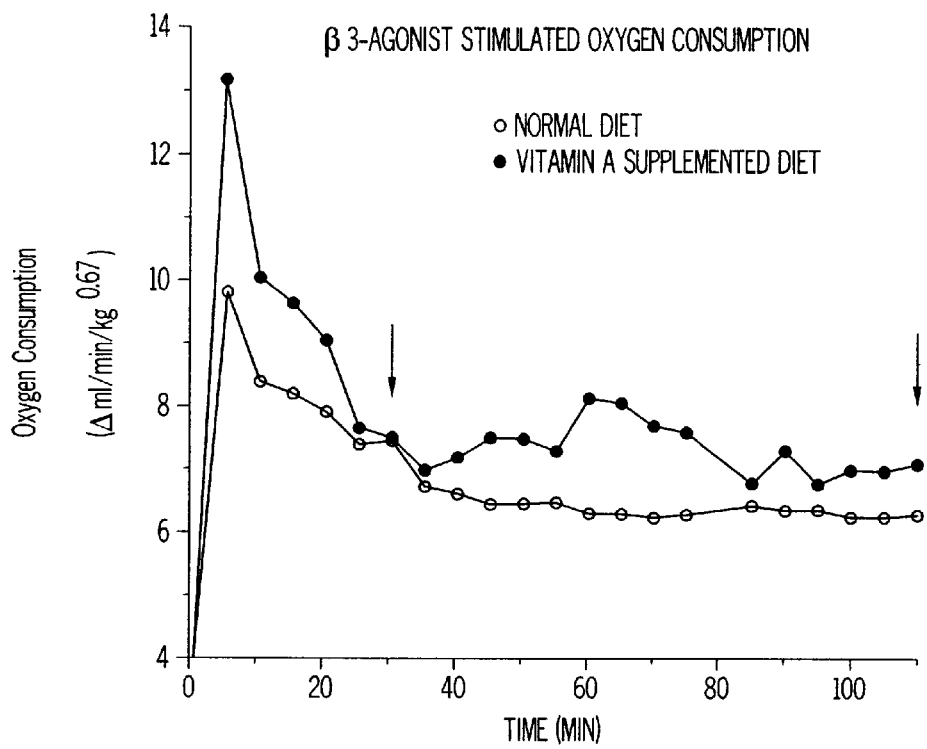
FIG. 3 is a graph of oxygen consumption ($\Delta$ml/min/$kg^{0.67}$) versus time for rats fed a normal diet or a Vitamin A supplemented diet.

To determine if there was an upregulation of the capacity for thermogenesis upon dietary vitamin A supplementation, the β3-adrenergic stimulated increase in oxygen consumption was measured in the two dietary groups at the end of the 8th week. Half the animals in the two dietary groups were administered either saline or the β3-adrenergic specific agonist, CGP-12177 (0.75 mg/kg, i.p.), and the increase in oxygen consumption measured. Upon administration of CGP-12177, there was a rapid and sustained increase in oxygen consumption in the rats on the normal and vitamin A supplemented diets, compared with the corresponding saline injected rats of the same dietary group. The averaged peak increase in the CGP-12177-stimulated oxygen consumption (calculated as the average increase over saline injection from 30 min to 110 min, postinjection) in the rats fed the vitamin A supplemented diet was 14% higher than in the rats fed the normal diet (FIG. 3).

UCP1 mRNA Levels in BAT

Figure 4:
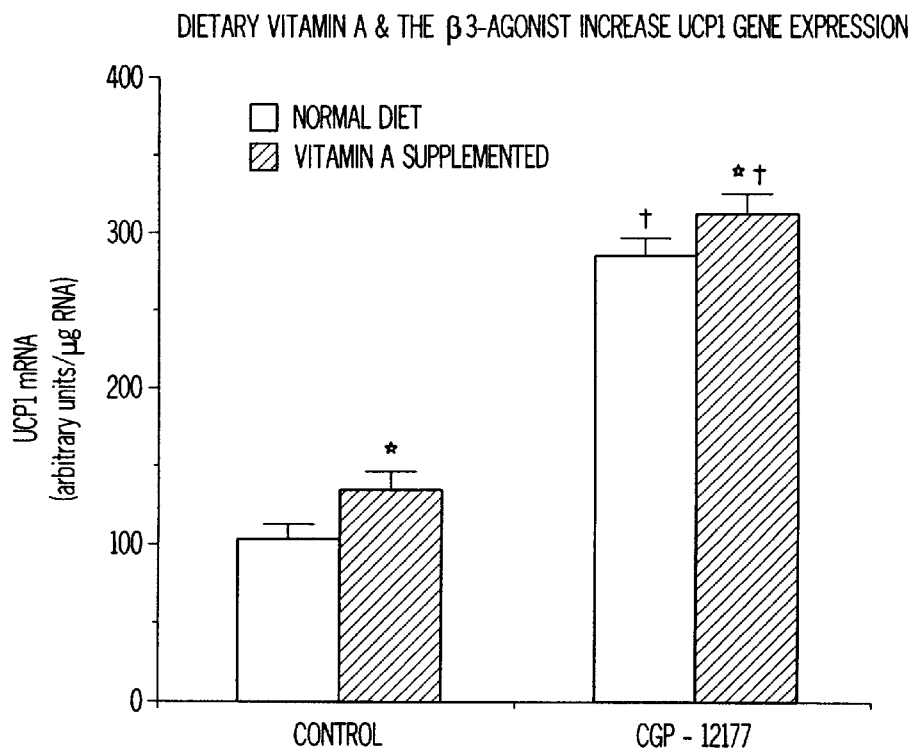
FIG. 4 is a graph of UCP1 mRNA levels (arbitrary units/$\mu$g RNA) for rats fed a normal diet or a Vitamin A supplemented diet.

To determine if the increase in β3-adrenergic stimulated oxygen consumption was associated with elevated UCP1 gene expression, the effects of vitamin A supplementation on UCP1 mRNA levels in BAT were determined by comparison of UCP1 mRNA levels in rats on the vitamin A supplemented and normal diets. There was a 31% increase in UCP 1 mRNA levels upon dietary vitamin A supplementation (FIG. 4). To assess if there was an increased capacity to respond to β3-adrenergic agonist stimulation in the dietary vitamin A supplemented rats, changes in UCP1 mRNA levels were compared in the CGP-12177 administered animals on the vitamin A supplemented and normal diets. Upon administration of CGP-12177, there was a significant but similar increase in UCP1 mRNA levels in rats on both the vitamin A supplemented and normal diets (FIG. 4). There were no changes in the levels of β actin mRNA in BAT in the saline or CGP-12177 treated animals in the two dietary groups (Table 4, above).

UCP2 mRNA Levels in BAT and PWAT

To determine if increases in the gene expression of UCP2 could have also contributed to the increase in CGP-12177-stimulated oxygen consumption in vitamin A supplemented animals, UCP2 mRNA levels were measured in PWAT and BAT. There were no changes in the levels of UCP2 mRNA in PWAT between the two dietary groups (Table 4, above). Furthermore, treatment with CGP 12177 had no effect on the levels of UCP2 mRNA in PWAT in either of the two dietary groups of animals. Similar to PWAT, there were no changes in UCP2 mRNA levels in BAT, in any of the four experimental groups (Table 4).

β$_3$-adrenergic Receptor mRNA Levels in PWAT and BAT

To determine if the increase in β3-adrenergic stimulated oxygen consumption or suppression of leptin mRNA level was associated with an increase in β3-adrenergic receptor gene expression, the effects of vitamin A supplementation on β3-adrenergic receptor mRNA levels were measured in BAT and PWAT. There were no changes in the levels of β3-adrenergic receptor mRNA in either the saline or CGP-1 2177 treated animals on either the normal or vitamin A supplemented diet (Table 4). Similarly, in BAT, there were no changes in the levels of β3 adrenergic receptor mRNA in the saline treated animals on the vitamin A supplemented diet compared with the normal diet (Table 4). Upon treatment with CGP-12177 for 4 h, there was a similar (50%) down regulation of 133-adrenergic receptor mRNA levels in animals on the vitamin A supplemented and normal diets, compared with the corresponding saline treated animals from the two dietary groups (Table 4).

The results demonstrate that dietary vitamin A supplementation decreases adiposity in rats. This decrease in adiposity was associated with an increase in UCP1 gene expression but a decrease in a leptin gene expression. The decrease in adiposity was not associated with any change in food consumption suggesting it was a result of a redistribution of body composition or an increase in energy expenditure. Basal levels of whole body oxygen consumption were unchanged with dietary vitamin A supplementation, but β3-adrenergic stimulated oxygen consumption was greater in the rats supplemented with vitamin A compared with those on a normal diet. This suggests that the capacity for nonshivering thermogenesis in BAT was increased in the vitamin A supplemented rats.

Thermogenesis in BAT is mediated by norepinephrine activation of sympathetically innervated β3-adrenergic receptors. The β3-adrenergic signal transduction pathway serves both to activate BAT mitochondrial UCP1 and induce new synthesis of this protein. Activated UCP1 uncouples mitochondria, allowing high rates of substrate oxidation and heat production without phosphorylation of adenosine 5' diphosphate. The demonstration of an increase in basal UCP1 gene expression following dietary vitamin A supplementation suggests an upregulation in the capacity for thermogenesis in BAT. Furthermore, the increase in β3-adrenergic stimulated oxygen consumption suggests that an increase in energy expenditure may be contributing to the decrease in adiposity following dietary vitamin A supplementation.

In addition to β3-adrenergic agonists, leptin is another agent that increases thermogenesis in BAT. The most dramatic changes observed following dietary vitamin A supplementation were decreases in both serum leptin and leptin gene expression in PWAT. These changes were not consistent with either the decrease in adiposity or the increase in UCP1 gene expression. Leptin administration decreases food intake and increases energy expenditure. Despite the fall in serum leptin, food intake was unchanged and energy expenditure was increased. While not wishing to be bound by any particular theory, the leptin-induced increase in energy expenditure is believed to be a result of an increase in sympathetic nerve activity to BAT resulting in an increase in UCP1 gene expression. However, despite the fall in serum leptin, UCP1 gene expression increased.

Along with UCP1, the effect of vitamin A supplementation was examined on another transcript that may be involved in energy balance, UCP2. This uncoupling protein has 59% homology with UCP1 and 73% homology with UCP3. Similar to UCP1, UCP2 can partially uncouple mitochondrial respiration. The expression of UCP2, unlike UCP1, is not limited to BAT, and this protein is widely expressed in many tissues, including WAT, heart, and muscle in both rodents and humans. This experiment found no changes in UCP2 gene expression in PWAT with dietary vitamin A supplementation.

The salient findings of decreased adiposity, increased UCP1 gene expression, and decreased leptin gene expression are similar to what is observed following administration of a β3-adrenergic agonist. β3-adrenergic agonists suppress leptin gene expression in white adipose tissue, greatly enhance UCP1 gene expression in BAT, and decrease adiposity in rats. Thus, one possibility is that the effects of vitamin A supplementation may be mediated by enhanced β3-adrenergic responsiveness. No conclusive evidence of enhanced β3-adrenergic reactivity in the vitamin A supplemented rats was found, however. In BAT, β3-adrenergic receptor gene expression was unchanged with vitamin A supplementation. UCP1 gene expression was unchanged with vitamin A supplementation. UCP1 gene expression was elevated in vitamin A supplemented rats but this was most likely a direct result of retinoic acid, an active metabolite of vitamin A. It has been previously demonstrated that retinoic acid administration increases UCP1 gene expression. This induction is mediated by a retinoic acid-responsive element in promoter region of the UCP1 gene. Vitamin A and β3-adrenergic agonist induced increases in UCP1 gene expression following CGP-12177 stimulation was the same in rats on both the normal and vitamin A supplemented diets. In white adipose tissue, there was also no change in β-adrenergic receptor mRNA levels with vitamin A supplementation. In contrast, the suppression of leptin gene expression by the vitamin A supplemented diet could be the result of enhanced β3-adrenergic reactivity. Suppression of leptin gene expression by the vitamin A supplementation and by β3-adrenergic agonist administration were not additive. Moreover, in the vitamin A supplemented rat, there was no further decrease in leptin gene expression with CGP-12177 administration. This suggests that the two treatments share a common mechanism or that with vitamin A supplementation, the leptin gene expression is suppressed to maximum extent possible and that further suppression by β3-adrenergic stimulation is ineffective.

It also was found that basal whole body oxygen consumption was unchanged by the vitamin A supplemented diet, however, β3-adrenergic stimulated oxygen consumption was increased. The latter could represent enhanced β3-adrenergic function or could reflect the vitamin A-induced increase in UCP1 gene expression. Collectively, these data suggest that the effects of vitamin A on adiposity, UCP1 and leptin gene expression are not due to increases in endogenous stimulation of β3-adrenergic receptors, but the increased oxygen consumption in response to CGP-12177 and the failure of this β3-adrenergic agonist to suppress leptin gene expression in the vitamin A supplemented rat may involve altered β3-adrenergic signal transduction in BAT and PWAT.

The decrease in adiposity with vitamin A supplementation was highly significant (9%). This amount of decrease was surprising considering these were young lean F-344×BN rats that are not prone to obesity. More surprising, is that this decrease in adiposity was despite the greater than 65% decrease in serum leptin. Moreover food intake was unchanged. This suggests that leptin may not be the primary regulator of food intake or energy expenditure under these conditions. Furthermore, vitamin A supplementation may provide a convenient method to reduce serum leptin under conditions where it is abnormally elevated. Both obesity and the increase in body weight with aging are associated with elevated levels of serum leptin and leptin resistance. Moreover, the increased levels of leptin with obesity may be contributing to the diabetes caused by obesity. Recent studies have indicated that leptin may impair insulin action. Leptin inhibits the basal and glucose mediated insulin secretion from isolated pancreatic islets of both normal rats and ob/ob mice. Leptin also impairs the metabolic action of insulin in isolated rat adipocytes including glucose transport and lipogenesis. It has been indicated that leptin inhibits insulin signal transduction in human hepatic cells. However, this inhibition could not be duplicated in a hepatic cell line transfected with the leptin receptor. Thus, the elevated leptin levels in obese individuals may be harmful. Vitamin A supplementation may be one method to restore both leptin and insulin responsiveness under conditions of obesity and elevated serum leptin.

In summary, the data show that dietary vitamin A supplementation decreases adiposity, increases β3-adrenergic stimulated oxygen consumption and UCP1 gene expression in BAT, and suppresses leptin gene expression and serum leptin levels. Thus, dietary vitamin A supplementation has a role as an anti-obesity treatment or as one method to lower abnormal elevated serum leptin levels in animals.

EXAMPLE 2

Figure 5:
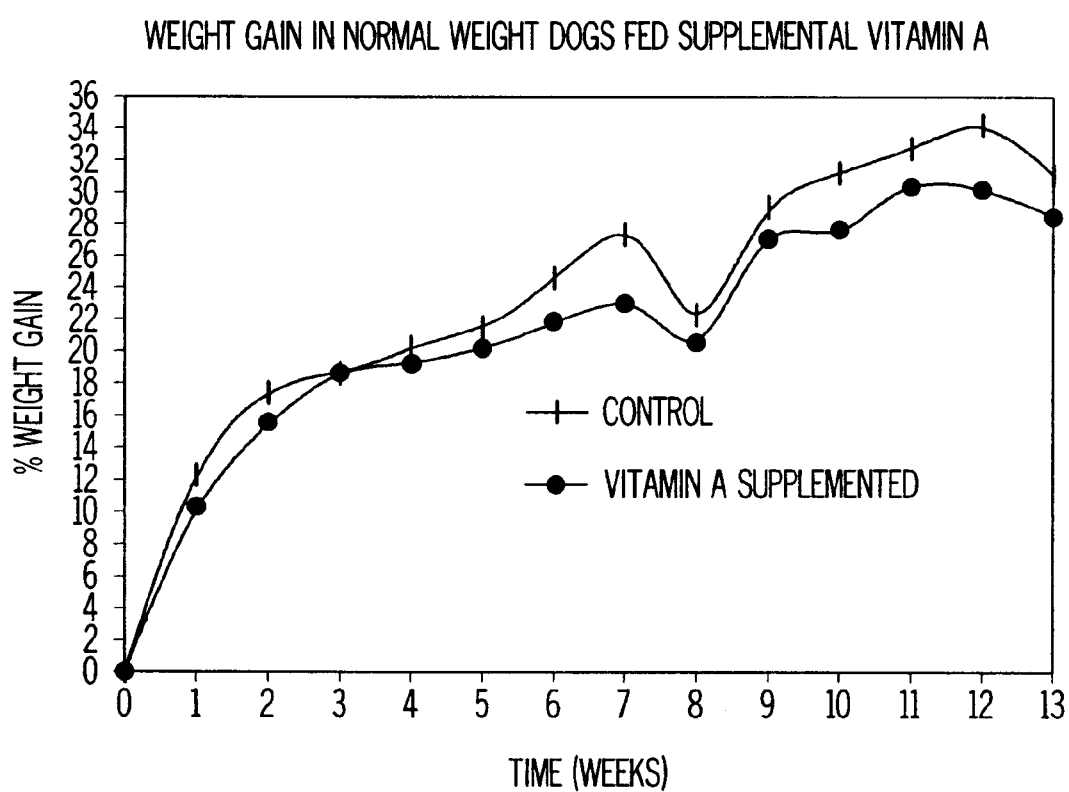
FIG. 5 is a graph showing weight gain in normal weight dogs fed Vitamin A.

To evaluate the influence of high amounts of vitamin A in the diet of dogs, an experiment was designed utilizing normal weight (12.1 kg) beagles. Thirty dogs were fed a diet minimally sufficient in vitamin A (9 KIU/kg) for two months. The dogs were then divided into two groups. Each group was fed one of two diets that contained a high amount of fat (24.4% DMB). The only difference in the diets was the amount of vitamin A (control=9 KIU/kg vs. high vitamin A=129 KIU/kg). The animals were allowed to consume these diets free choice for a 13-week period. Animals' body weights were assessed weekly and food intakes were assessed daily. Body composition was assessed using dual energy x-ray absorptiometry just before, during, and after consuming the high fat diets. Animals fed the high vitamin A diet gained less weight than the control fed animals (FIG. 5). High vitamin A consumption helped decrease body fat while maintaining muscle mass (Table 5). As can be seen from the table, body fat tends to decline and lean body mass increases as animals are fed increased amount of vitamin A. These results demonstrate the value of feeding increased vitamin A to help remove body fat (i.e., reduce adiposity) and prevent obesity.

TABLE 5

Body Composition of Dogs Fed Control or Supplemental Vitamin A

| Diet | Time Measured | Body Fat (%) | Lean Body Mass (%) | Bone Mineral Content (%) |
|---|---|---|---|---|
| Control | Baseline | 30.9 | 67.3 | 1.8 |
| High Vitamin A | Baseline | 31.4 | 66.8 | 1.8 |
| Control | Mid-point | 41.7 | 56.7 | 1.6 |
| High Vitamin A | Mid-point | 40.8 | 57.6 | 1.7 |
| Control | End | 44.3 | 54.2 | 1.6 |
| High Vitamin A | End | 43.1 | 55.3 | 1.6 |

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for reducing adiposity of a companion animal comprising the step of feeding said companion animal an effective amount of Vitamin A for a time sufficient to reduce adiposity in said companion animal.

2. A process as claimed in claim 1 in which said Vitamin A is fed to said companion animal as a supplement in an amount of about 50,000 IU to about 1,000,000 IU of Vitamin A per day.

3. A process as claimed in claim 1 in which said Vitamin A is fed to said companion animal as a supplement in an amount of about 5,000 IU to about 100,000 IU of Vitamin A per day.

4. A process as claimed in claim 1 wherein said companion animal is a horse.

5. A process as claimed in claim 1 wherein said companion animal is a dog.

6. A process as claimed in claim 1 wherein said companion animal is a cat.

7. A process for reducing adiposity of a companion animal comprising the step of feeding said companion animal a diet containing an effective amount of Vitamin A for a time sufficient to reduce adiposity in said companion animal.

8. A process as claimed in claim 7 in which said diet includes from about 50,000 IU to about 1,000,000 IU of Vitamin A per kilogram of diet.

9. A process as claimed in claim 7 in which said diet comprises about 18 to 40% crude protein, about 4 to 30% fat, and about 4 to 20% total dietary fiber.

* * * * *